United States Patent [19]

Dellinger

[11] Patent Number: 4,526,540
[45] Date of Patent: Jul. 2, 1985

[54] ORTHODONTIC APPARATUS AND METHOD FOR TREATING MALOCCLUSION

[76] Inventor: Eugene L. Dellinger, 1326 Old Lantern Ter., Ft. Wayne, Ind. 46825

[21] Appl. No.: 562,858

[22] Filed: Dec. 19, 1983

[51] Int. Cl.³ .............................................. A61C 7/00
[52] U.S. Cl. ........................................... 433/24; 433/6
[58] Field of Search ....................................... 433/24, 2

[56] References Cited

U.S. PATENT DOCUMENTS 3,738,005  6/1973  Cohen et al. ........................... 433/24

Primary Examiner—Robert Peshock
Attorney, Agent, or Firm—George A. Gust

[57] ABSTRACT

The invention comprehends the use of a fixture which fits over a tooth on which a bracket is to be affixed, this fixture having an internal cavity which matches the shape and contour of a portion of the tooth, such as the lingual surface, incisal edge and a portion of the labial surface. A second portion of the labial or lingual side of the fixture is fixedly secured to the head portion of the bracket in such a manner as to align the surface of the base in the same anatomical plane or tooth surface as the labial or lingual surface. The fixture is relatively rigid and is further of a material which can be changed to a non-rigid state upon application of a state-changing medium thereto. Such a material may be biodegradable such that upon being subjected to moisture, it tends to dissolve or become flexible: it can then be easily removed from the bracket. Removal from the bracket is performed after the fixture with the bracket mounted therein is assembled to a tooth and the bracket is bonded thereto.

By forming the fixture with the bracket preassembled thereto, the assembly can be used to bond a bracket on the patent's tooth in a precise predetermined location.

19 Claims, 6 Drawing Figures

ORTHODONTIC APPARATUS AND METHOD FOR TREATING MALOCCLUSION

BACKGROUND OF THE INVENTION

1. Field of the Invention

The present invention relates to orthodontics and more particularly to a method and apparatus useful in precisely locating a bracket on a patient's tooth in optimal position.

2. Description of the Prior Art

Prior art methods and apparatuses for precisely locating brackets on patient's teeth are disclosed in U.S. Pat. Nos. 3,738,005, 3,949,478, 4,014,096, 4,160,322, 4,183,141 and 4,360,341. Some of these patents disclose the use of procedures for the precise and correct placement of brackets upon the teeth utilizing idealized laboratory models. Brackets are mounted on the model in positions which conform to an idealized coplanar arch wire, while in others, prefabricated brackets are ideally located on the model and eventually incorporated into a transfer mask conforming to the malocclusion for placement on the patient's teeth. In still other of such patents, bracket-holding devices are incorporated into transfer masks adapted to be registered over patient's teeth. The bracket-holding devices or portions thereof serve in locating the brackets on the teeth in positions corresponding to those selected on the model. In Cohen et al U.S. Pat. No. 3,738,005, there is disclosed the forming of a bracket-retaining mold which is of flexible, self-sustaining, resilient character that has been molded into positive, capturing engagement with the brackets. In following this procedure, one of the first steps is to make a dental cast of the patient's malocclusion. Brackets are applied to the tooth replicas by the orthodontist in desired locations. A bracket-retaining mold is formed over the dental cast having the brackets mounted thereon. This results in providing an arch shaped transfer device which is then used to carry the brackets to the patient's mouth where the brackets are bonded into position. The flexible transfer device or positioner is then flexed off the brackets and teeth leaving the brackets in place.

In Schinhammer U.S. Pat. No. 3,949,478, the procedure is similar to that just described except an idealized model is fabricated and brackets are removably secured to the tooth replicas in coplanar position. These replicas with mounted brackets are then removed from the model and placed in a jaw model of the patient's malocclusion. There is then formed an arch shaped mold or transfer device of elastic material for carrying the brackets to the patient's mouth. Since this mold is elastic, it may be peeled or flexed off the patient's teeth and brackets the same as described above.

In the Dellinger U.S. Pat. No. 4,360,341, an arrangement similar to that of the foregoing two patents is disclosed to the extent of using a flexible fixture or transfer device for applying the brackets to the teeth in the patient's mouth.

SUMMARY OF THE INVENTION

The present invention relates to an apparatus and method by means of which brackets may be easily and precisely located and affixed to a patent's teeth in accordance with a fixed standard. This standard may be customized as to a particular patient or established by one of a series of typical case setups. This invention finds particular utility in a technique in which the slots of the brackets are predetermined on an idealized laboratory model, and are coplanar. When treatment of the patient is completed, the bracket slots are coplanar according to the slot arrangement on the idealized model. This generally corresponds to prior art methods and apparatuses.

In one method of this invention, the bracket is positioned on the patient's tooth precisely as predetermined according to the steps of forming a model for the patient's teeth in the shape of a dental arch with the replicas of the teeth ideally located. Brackets are releasably mounted on selected replicas in preselected locations. A fixture of a formable material is formed over the dental arch into intimate conformity with the crowns, the lingual and labial surfaces and onto the brackets in securing engagement therewith. The fixture is formed of a material which after being formed is relatively rigid but can be subsequently altered as to its physical properities to facilitate removal thereof from the brackets as well as the patient's teeth.

The replica configuration of the fixture is utilized to locate and bond the bracket onto the corresponding tooth in the patient's mouth. Once mounted, the physical properties of the utilized fixture are altered for facilitating removal thereof from the patient's teeth and the brackets.

In a specific embodiment of the foregoing arrangement, the material of the fixture is biodegradable and is intimately conformed about the head portion of the bracket, this material changing state into a non-rigid, flexible condition when subjected to moisture, which presents little resistance to the practitioner in picking it off the patient's tooth and bracket.

Further features of the invention reside in the use of an adhesive for securing releasably the brackets to the tooth replicas such that after the mold or fixture is formed over the brackets, the fixture and replicas as an integrated assembly can be bodily snapped or released from the replicas in such a manner that the portion of the adhesive contiguous with the tooth retains the precise surface contour thereof. When the bracket is transferred to the patient's tooth, that same exposed surface will then essentially precisely match the corresponding attachment area on the tooth.

It is an object of this invention to provide a method and apparatus which facilitates treatment of malocclusion.

It is another object of this invention to provide a method and apparatus for positioning brackets onto teeth with a high degree of precision.

The above-mentioned and other features and objects of this invention and the manner of attaining them will become more apparent and the invention itself will be best understood by reference to the following description of an embodiment of the invention taken in conjunction with the accompanying drawings.

DESCRIPTION OF THE PREFERRED EMBODIMENT

In practicing the present invention, an idealized model of the patient's teeth is produced in accordance with conventional practice and otherwise as disclosed in Dellinger U.S. Pat. Nos. 4,014,096 and 4,360,341. A coplanar line or mark 12 is drawn on the tooth replicas 14. The position of the line 12 on each replica 14 is selected by the practictioner to coincide with the desired location of the slot in a bracket to be directly bonded to the replica. The line 12 around the entire dental arch will correspond to the shape of an arch wire, preferably smoothly curvilinear and coplanar, to be used in the final stages of treatment. Other line patterns may be used without departing from the spirit and scope of this invention.

Suitable brackets 18 are bonded to the replicas 14 with the slots in registry with the line 12. While the bonding adhesive is conventional, it is of such character that it releasably mounts the brackets onto the replicas, adhering to the bracket more strongly than the replica. The adhesive in liquid or semi-liquid form is first applied to the attachment area on the labial or buccal surface of the replica, additional adhesive is provided on the mounting surface of the bracket base, following which the bracket is pressed onto the replica in the precise location desired for a short period of time until the adhesive cures to the point at which it retains the bracket in place. At this point, there will be excessive adhesive material which has flowed out from the edges of the bracket base, and this must be cleaned away. A suitably sharp instrument is used for the purpose, thereafter the adhesive is allowed to fully cure.

Figure 1:
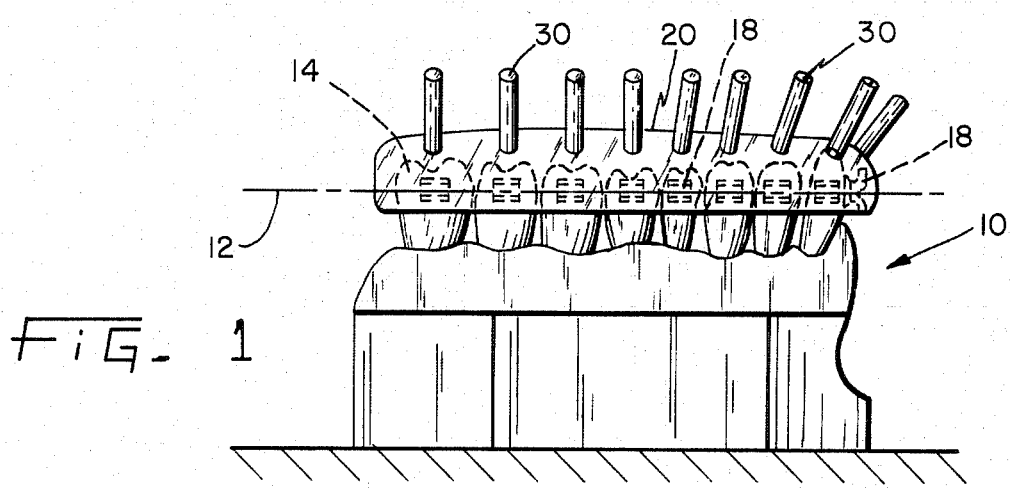
FIG. 1 is a side elevation of an idealized model of a dental arch illustrating one portion of the method of this invention.
Figure 2:
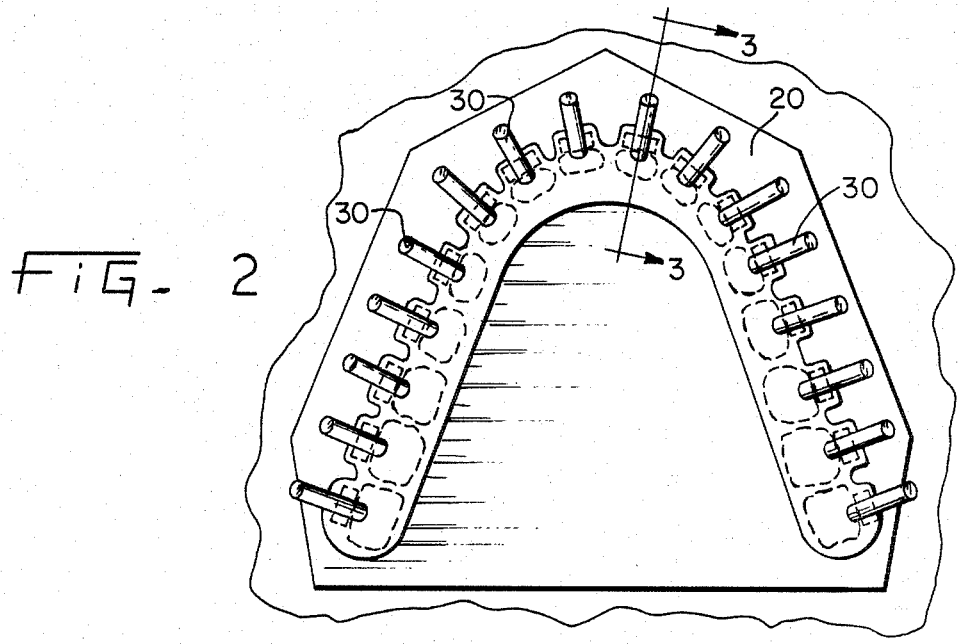
FIG. 2 is a top plan view thereof.
Figure 3:
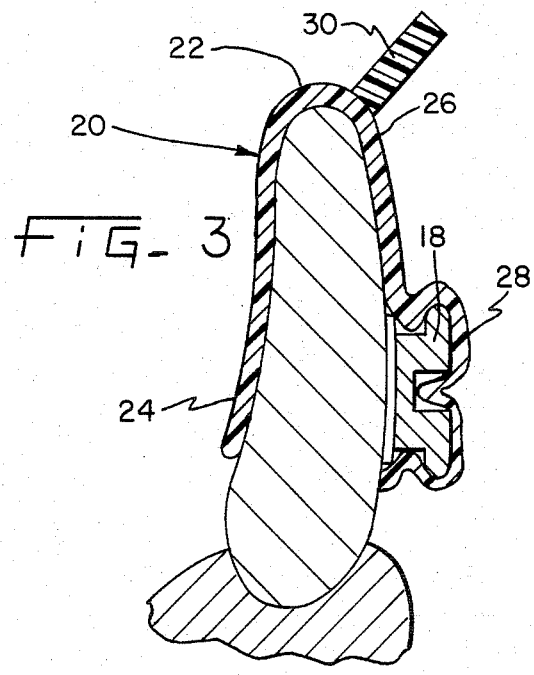
FIG. 3 is an enlarged sectional view taken substantially along section line 3—3 of FIG. 2.

With the brackets so bonded to the replicas, a plastic cap or fixture 20 having the shape of the idealized model is formed over the replicas 14 and the brackets 18 mounted thereon. The fixture 20 intimately engages the incisal edges, the lingual surfaces and portions of the labial surfaces as indicated by the references numerals 22, 24 and 26, respectively. The fixture thus has lingual, labial and incisal portions conforming to the surface anatomy of the corresponding portions of a patient's tooth. Further, the fixture 20 as molded over the bracket 18 (FIG. 3) intimately conforms to the undercuts and slots. This portion of the fixture 20 is indicated by the numeral 28. In the portion 28, the material substantially encompasses and locks the bracket 18 in position.

In a working embodiment, in which the material of the fixture 20 is a biodegradable film, a small amount of silicone adhesive is first applied to the labial surface of the bracket 18 for further adhering and locking of the bracket 18 in place.

The material of the fixture 20 preferably is plastic and may be in liquid, semi-liquid or solid film form. In a preferred arrangement, this material is a solidified biodegradable film which is heat moldable to be vacuum formed over the replicas and brackets. After being so formed, the material hardens. Once hardened, the fixture is for all practical purposes rigid, the antithesis of being flexible, resilient or elastic.

Figure 5:
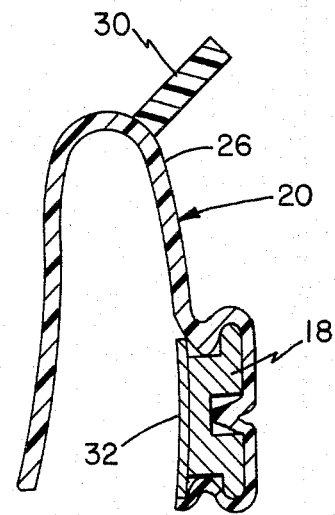
FIG. 5 is a sectional view like that of FIG. 3 of the fixture unit with the bracket attached just prior to being transferred to a patient's tooth.

The fixture 20 and the encapsulated brackets 18 now constitute an integrated assembly which is releasably adhered to the model replicas. While still adhered, little handles 30 are attached by glueing or otherwise to the incisal edge portions of the fixture in registry with each replica as shown in the drawings. After the various adhesives and materials have completely cured and hardened, the fixture-bracket assembly 18, 20 is merely withdrawn from the replicas simply by manually picking or forcing the brackets loose. Since the adhesive used is more releasable from the replica than it is the bracket, the adhesive will separate from the replica leaving an imprint on the exposed surface of the adhesive area which intimately conforms to that of the attaching surface of the replica, hence the patient's tooth. This adhesive then becomes a part of the bracket and serves as a contoured shim whereby the bracket may be intimately fitted to the corresponding patient's tooth. Once removed, the fixture-bracket assembly 18, 20 appears as shown in FIG. 5 (for a single tooth or replica) with the exposed surface 32 of the bracket base serving as an anatomical extension of the inner surface of the labial portion 26 of the fixture 20. The fixture 20 is quite rigid, and once removed from the replica, it will have interior shapes corresponding to that of the respective replicas.

At this point it is necessary to make certain that the surface 32 on the bracket base is chemically clean. This is accomplished by blasting with an inert gas, such as nitrogen to an extent as will clean the surface for bonding to a patient's tooth.

Figure 4:
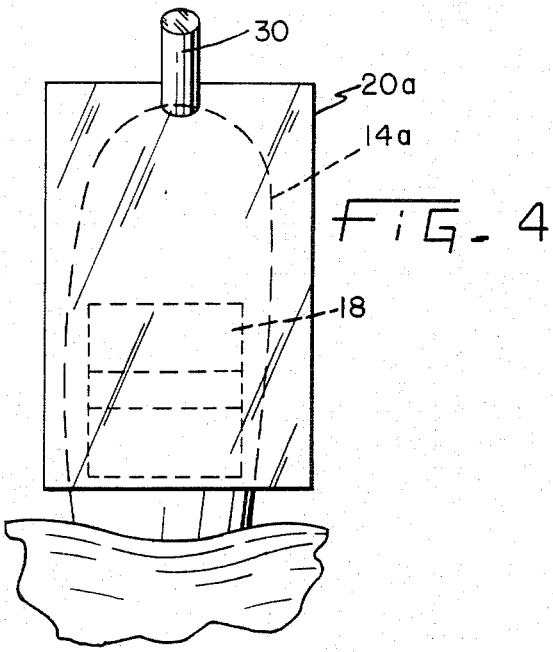
FIG. 4 is a labial view of the arrangement of FIG. 3.

The integrated arch-shaped fixture-bracket assembly 18, 20 is now sectioned into units, one for each replica 14. Each fixture unit 20a (See FIG. 4) may now be used to transfer a bracket 18 to the corresponding tooth 14a in the patient's mouth. The fixture 20a is now fitted over the corresponding tooth of the patient with the lingual, incisal and labial cavity portions fitting precisely, or in other words conforming to the surface anatomy of, the corresponding shape and irregularities of the tooth. Since the bracket 18 is positively oriented with respect to the fixture unit 20a, the bracket 18 will be positioned on the patient's tooth in precisely the same position as it was on the replica.

Bonding of the bracket to the tooth is accomplished by applying cement to the tooth or bracket base before the fixture unit is applied to the tooth. The fixture unit 20a is held in position until the cement cures. Since the fixture unit 20a is quite rigid, once the fixture is applied to the tooth, the bracket 18 is automatically and precisely positioned with respect to the tooth. Stated in other words, since the fixture 28 is not flexible, resilient nor elastic the fitting of the fixture 20a over the tooth does not result in undesired movement laterally or otherwise of the bracket 18. In this connection, the manipulation of the bracket fixture 20a is facilitated by grasping the handle 30.

Since the material of the fixture 20a completely encircles and grips the bracket 18, and since the material is relatively rigid, it is, for all practical purposes, essentially non-removable from the bracket 18. However, the material of the fixture 20a is so selected that it can be altered in its physical properties from, for example rigid to non-rigid, rigid to flexible, dissolvable, etc. By making the fixture of a film of biodegradable material, subjecting the fixture while mounted in the patient's mouth and after the bracket 18 has become bonded to the tooth, to moisture such as the saliva in the patient's mouth or a spray of water, the fixture tends to soften, become pliable or flexible following which it may be simply manually picked off the bracket and thereby removed from the patient's tooth. Brackets are applied to all of the patient's teeth in the same manner, there being an individualized unit 20a for each tooth.

Figure 6:
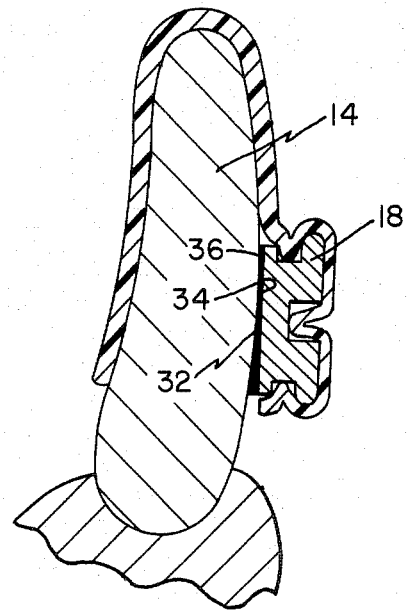
FIG. 6 is a view similar to that of FIG. 3 illustrating in exaggerated form the method of shimming and conforming the base of the bracket to an attachment area on the patient's tooth.

Further exemplification of the temporary attachment of the bracket 18 to the replica 14 and the formation of a contoured shim is illustrated in FIG. 6. In this figure the bottom surface 34 of the bracket 18 is shown to be shaped somewhat reversely with respect to the tooth surface. The adhesive is indicated by the numeral 36 as filling the space between the bracket and the replica. Once the adhesive hardens, a surface like the surface 32 remains which will conform to the corresponding portion of the patient's tooth. The reversely shaped surface 34 permits use of the same bracket for mounting on teeth of almost all surface contours, the adhesive serving as a filler for completing the shaping of the bracket base for fitting the patient's tooth. The biodegradable film used in a working embodiment of this invention is essentially a flat sheet or film which is self-supporting and preferably square in shape. The material of the film is polyvinylalchohol, for example. It measures four inches on a side and is approximately eight to twelve mils thick. It may be used in conventional vacuum-forming equipment wherein heat is applied to the film at the time it is being vacuum formed over the replicas. Other materials may, of course, be used so long as the finished fixture is relatively rigid and can be altered in its physical properties from a rigid condition to one that is pliant, flexible or in other words non-rigid so that it may be conveniently and easily removed from the bracket once it has been mounted on the patient's tooth.

The individualized fixtures 20a are light in weight, diminutive, and non-bulky thereby facilitating manipulation for quick, easy, accurate installation. By being rigid the fixture enables direct bonding in a precise pre-selected position which, in utilizing the preferred technique described earlier, permits finished treatment by means of a pre-configured, coplanar archwire. Since the fixtures 20a are individualized, one for each tooth, they are individually useable irrespective of any anatomical changes as to other teeth. This is better understood by comparing with known positioners which are arch shaped to fit a patient's total malocclusion (See Cohen et al U.S. Pat. No. 3,738,005 and Shinhammer U.S. Pat. No. 3,949,478). Any change in any one tooth, for example, as to position, size, etc., renders the positioner unuseable since it no longer fits the one tooth hence it cannot fit over the remaining teeth.

Since the bracket-locating fixtures of this invention are custom fabricated for the individual patient, free hand placement and many of the judgment factors involved on the part of practitioner are eliminated. Accuracy in bonding location coupled with a savings in practitioner's time can indeed provide for improved treatment at lower costs.

Summarizing, the invention broadly involves transporting the bracket to the mouth by means of a relatively rigid fixture or appliance, bonding the bracket in place, and then altering the material of the fixture from rigid to flexible, for example, to facilitate removal of the fixture from the bracket.

While there have been described above the principles of this invention in connection with specific apparatus, it is to be clearly understood that this description is made only by way of example and not as a limitation to the scope of the invention.

What is claimed is:

1. Apparatus for positioning a bracket onto a patient's tooth comprising a rigid locating fixture having an internal cavity provided with lingual and labial sides and an incisal edge portion therebetween; said fixture being of a plural-state material which in one state is rigid and in a second state is non-rigid, dissolved, flexible, soft or pliable, said material being alterable from said one to said second state by the application of a state-changing medium thereto, said lingual side, incisal edge portion and a first portion of said labial side conforming to the surface anatomy of the corresponding portions of a patient's tooth, a bracket having head and base portions, a second portion of either said labial or lingual side while in said one state being fixedly secured to and not removeable from the head portion of said bracket with the latter being in such position as to orient said base in the same anatomical surface as said first portion of said labial or lingual side.

2. The apparatus of claim 1 wherein said fixture in said one state is secured to said head portion by intimately encompassing the same.

3. The apparatus of claim 2 wherein said bracket is further secured to said fixture by means of releaseable adhesive.

4. The apparatus of claim 2 wherein the material of said fixture is biodegradable.

5. The apparatus of claim 1 wherein the material of said fixture is is biodegradable.

6. The apparatus of claim 1 wherein said fixture is of a size to fit only a single patient's tooth of a patient.

7. The apparatus of claim 6 wherein the attaching surface of said bracket base has a hardened body formed of liquid adhesive material secured thereto having an exposed attaching surface which conforms substantially precisely to the contour of the corresponding attaching area of the labial side of the aforesaid patient's tooth.

8. The apparatus of claim 6 including a handle secured to said fixture for grasping by a practitioner during installation into a patient's mouth.

9. The apparatus of claim 8 wherein said handle is elongated and is attached at one end to the fixture near the incisal-labial portions thereof.

10. The apparatus of claim 1 including means in addition and attached to said fixture for grasping by a practitioner to facilitate manual manipulation of said fixture.

11. The method of fabricating an orthodontic appliance and re-positioning a patient's teeth, comprising the steps of:
 forming a model of the patient's teeth in the shape of a dental arch with the replicas of the individual teeth ideally located,
 releaseably mounting brackets on selected tooth replicas in preselected locations,
 forming a rigid fixture over the dental arch in intimate conformity with the respective replica crowns, lingual and labial surfaces and said brackets in securing engagement with the latter, said fixture being of a plural-state material which after being so formed is in a rigid state intimately secured to said brackets and not removeable therefrom without altering such rigid state, said material being alterable to another state which is non-rigid, dissolved, flexible, softened or pliable, to facilitate removal thereof from said brackets, removing portions of said fixture along with said brackets while in said rigid state from said dental arch, utilizing the rigid fixture portions with such brackets secured thereto to locate the respective brackets onto the corresponding teeth in the patient's mouth, bonding said brackets onto such teeth while so located, and altering the physical properties of the utilized fixture portions while in the patient's mouth to said other state for removal of said portions from the patient's teeth and said brackets.

12. The method of claim 11 including the step of dividing selected portions of said fixture into rigid units, one unit for each tooth replica, each unit having a bracket secured therein, and fitting said rigid units with the respective brackets therein over the corresponding teeth in the patient's mouth for locating the brackets thereon.

13. The method of claim 12 wherein the brackets on the replicas have undercut portions between the heads and bases thereof, the step of forming said fixture causing the material thereof to enter said undercut portions thereby to secure said brackets in position on said fixture.

14. The method of claim 12 including the step of using adhesive to further secure said brackets to said fixture.

15. The method of claim 13 including the step of using adhesive to further secure said brackets to said fixture.

16. The method of claim 11 wherein the material of said fixture is biodegradable and after mounting on the patient's tooth and upon the application of moisture becomes less rigid and thereby removable from said brackets and teeth.

17. The method of claim 11 wherein the mounting of brackets on selected replicas is accomplished by means of an adhesive which adheres to the brackets with more force than to the replicas whereby the fixture-bracket assembly may be removed from the model as a single unit.

18. The method of claim 17 wherein the undersurface of the bracket base does not conform to the contour of the replica in the area of attachment, said adhesive filling the gaps and spaces formed between such undersurface and replica, said adhesive further being of such character as to solidify and to separate from said replica flush with such area thereby leaving the remainder of the adhesive secured to the bracket to form a shimming piece which precisely fits the corresponding area on the tooth in the patient's mouth.

19. The method of claim 18 including the step of cleaning the exposed surface of the adhesive after separation from the replica and prior to installation in the patient's mouth.

* * * * *